United States Patent

McCain, Jr. et al.

[11] Patent Number: 5,162,578
[45] Date of Patent: Nov. 10, 1992

[54] ACETIC ACID FROM ETHANE, ETHYLENE AND OXYGEN

[75] Inventors: James H. McCain, Jr., Charleston; Steven W. Kaiser, South Charleston; George L. O'Connor, Charleston, all of W. Va.

[73] Assignee: Union Carbide Chemicals & Plastics Technology Corporation, Danbury, Conn.

[21] Appl. No.: 61,150

[22] Filed: Jun. 12, 1987

[51] Int. Cl.$^5$ .................................. C07C 53/08
[52] U.S. Cl. .................. 562/512.2; 562/548; 562/549
[58] Field of Search .............. 562/512.2, 548, 549

[56] References Cited

U.S. PATENT DOCUMENTS 4,250,346  2/1981  Young et al. ........................ 562/549

FOREIGN PATENT DOCUMENTS 720424  10/1965  Canada ................................ 562/548
46-6763  2/1971  Japan ................................. 562/548

Primary Examiner—Jose G. Dees
Attorney, Agent, or Firm—Sharon H. Hegedus

[57] ABSTRACT

A process for the higher selective production of acetic acid by the catalytic oxidation with oxygen of ethane, or ethylene, or mixtures thereof, in contact with a mixed catalyst composition containing (A) a calcined mixed oxides catalyst of the formula:

$$Mo_xV_yZ_z$$

wherein Z represents nothing or a metal from a group of metals as hereinafter defined and (B) is an ethylene hydration catalyst and/or an ethylene oxidation catalyst.

64 Claims, No Drawings

ACETIC ACID FROM ETHANE, ETHYLENE AND OXYGEN

FIELD OF THE INVENTION

This invention relates to the production of acetic acid by the catalytic oxidation of ethane, or ethylene, or mixtures of ethane and ethylene, with oxygen in contact with a mixed catalyst. The mixed catalyst contains: (A) an oxidation catalyst containing the metal elements molybdenum and vanadium in the form of their oxides, alone or with other metals, and (B) an ethylene hydration catalyst and/or an ethylene oxidation catalyst. The use of the mixed catalysts compositions in the processes of this invention produces acetic acid at unexpected and unpredictable higher levels of selectivity and productivity and with less recycle of ethylene than one would expect or predict based on knowledge available in the prior literature.

DESCRIPTION OF PRIOR ART

U.S. Pat. No. 4,250,346, issued to F. G. Young and E. M. Thorsteinson on Feb. 10, 1981, discloses a process for the oxydehydrogenation of ethane to ethylene using a calcined catalyst containing the elements $Mo_aX_bY_c$ in which X can be on or more of V, Nb and Mn, V and W, V and Mn or W and Nb; Y is Bi, Ce, Co, Cu, Fe, K, Mg, Ni, P, Pb, Sb, Si, Sn, Tl and or U and (a), (b) and (c) are as defined. The reference shows that some acetic acid is produced as a by-product. However, the reference does not suggest or disclose the use of the mixture of catalysts of this invention, nor of the specific feed introduced into the reactor, nor of the high selectivity to acetic acid achieved by the oxidation reaction of this invention. The reference is concerned with obtaining a high selectivity to ethylene.

U.S. Pat. No. 4,524,236, issued to J. H. McCain on Jun 18, 1985, is directed to the use of a calcined catalyst of the formula $Mo_aV_bNb_cSb_dX_e$ for the oxydehydrogenation of ethane to produce ethylene. During the process some acetic acid is produced as a by-product. Though the catalysts disclosed in this patent are one of the catalyst components present in the combination of mixed catalysts compositions used in the invention that is the subject matter of this application, U.S. Pat. No. 4,524,236 neither suggests nor discloses the use of the mixed catalyst compositions of this invention in the instant process for selectively producing acetic acid.

U.S. Pat. No. 4,568,790, issued to J. H. McCain on Feb. 4, 1986, discloses a process for the oxydehydrogenation of ethane to ethylene using a calcined catalyst of the formula $Mo_aV_bNb_cSb_d$. The process described is that of selectively oxydehydrogenating ethane to ethylene whereas the process of this invention is the oxidation of ethane, ethylene or a mixture of ethane, together with the formation of small amounts of acetic acid, and ethylene to selectively form acetic acid using a mixture of catalysts.

The above three patents make reference to other patents concerned with the production of ethylene from ethane by various oxydehydrogenation processes using different catalysts and all make reference to the formation of an acid as a by-product. However, none of these references suggest or disclose the oxidation process of this application that uses a mixture of catalysts.

Japan 57-102835, originally filed by T. Yamada and M. Toshikuni on Dec. 16, 1980, is concerned with a process for producing acetic acid from ethanol or acetaldehyde using a catalyst containing a copper oxide. The patent does not disclose our catalyst or our oxidation process of producing acetic acid from ethane and ethylene.

Japan 54-57488, originally filed by T. Kondo on Oct. 17, 1977, is concerned with the production of acetic acid by the oxidation of ethylene using a molybdovanadophosphoric acid modified with palladium. The catalyst had the structure [$NaPd_{0.5}H_2(PMo_{11}VO_{40})$]. A single catalyst entity was used, not a mixture.

Japan 46-6763, originally filed by Y. Nakanishi, N. Kurata and Y. Okuda on Mar. 14, 1968, is concerned with the catalytic oxidation of ethylene to yield mixtures of acetic acid, formic acid, acetaldehyde and carbon dioxide and other unidentified by-products. The specific catalysts disclosed in the examples contain the following combinations of metal atoms V-Pd-Sb; V-Rh-Sb; V-Pd-P; V-Rh-P; V-Pd-As;V-Rh-As; Mo-Pd-Sb; Mo-Rh-Sb; Mo-P-Pd; Mo-P-Rh; Mo-Pd-As; Mo-Rh-As and Mo-P-W-Pd-Rh-Sb. None of these correspond to the mixtures of two or more components as found in applicants' catalysts compositions.

Syoji Tan, Yoshihiko Moro-Oka and Atsumu Ozaki in "Catalytic Oxidation of Olefin over Oxide Catalysts Containing Molybdenum", J. Catal, 17, 132–142 (1970) report that olefins oxidize to the ketones over the binary catalyst systems $Co_3O_4$-$MoO_3$ and $SnO_2$-$MoO_3$. Though some acetic acid is formed as a by-product together with other compounds, the catalysts are generally selective to the ketone. In the first full paragraph in the second column on page 136 the authors report the product of the oxidation of ethylene was mainly carbon dioxide in all cases.

Masakazu Iwamoto, Masahiro Tajima and Shuichi Kagawa in "Gas-phase Hydration of Ethylene over a Proton-exchanged Ferrierite-type Zeolite Catalyst", J. Chem, Soc. Chem. Commun., 228–230 (1985) report on the hydration of ethylene to ethanol using the zeolites. The disclosure contains no mention or indication of acetic acid formation; nor does it use the oxidation catalyst MoVNbSbX Present in the catalyst combination employed by applicants. The Iwamoto et al. reference is a hydration reaction not an oxidation reaction.

Mamoru Ai in "The Oxidation Activity and Acid-Base Properties of $SnO_2$-Based Binary Catalysts", J. Catal., 40, 327–333 (1975) reports on the vapor phase oxidation of olefins using the binary catalyst systems $SnO_2$-$MoO_3$ and $SnO_2$-$P_2O_5$. There is nothing in this article suggesting SnMo oxide catalysts as useful for oxidation of ethylene and ethane to acetic acid.

In a subsequent article by Mamuro Ai, "The Activity of $WO_3$-based Mixed-Oxide Catalysts", J. Catal., 49, 313–319 (1977), he reported on the activity of the $WO_3$-$P_2O_5$ and $WO_3$-$P_2O_5$-$X_nO_m$ systems on the oxidation of olefins. He found that they are effective in the oxidation of butene and butadiene to maleic anhydride. In the second full paragraph of the first column on page 317 he reported that under the reaction conditions employed the W-P-X oxides catalysts are inactive with a feed of butene, air and water and neither acetic acid nor methyl ethyl ketone can be obtained with these catalysts.

The use of a MoVNb oxide catalyst system for the oxidative dehydrogenation of ethane to selectively produce ethylene was reported by E. M. Thorsteinson, T. P. Wilson, F. G. Young and P. H. Kasai in "The Oxidative Dehydrogenation of Ethane over Catalysts Containing Mixed Oxides of Molybdenum and Vanadium"

J. Catal., 52, 116-132 (1978). Along with the ethylene the authors found quantities of acetic acid and other by-products. However, this article does not suggest or disclose the process described in this instant application.

SUMMARY OF THE INVENTION

The present invention relates to a process for the selective production of acetic acid by reacting ethane, ethylene or mixtures of ethane and ethylene with oxygen over a catalyst mixture containing (A) a calcined ethane oxidation catalyst containing molybdenum and vanadium and which may optionally contain at least one other metal atom as represented by the general formula $Mo_xV_yZ_z$ in which the metal elements are in combination with oxygen in the form of various oxides and (B) an ethylene hydration catalyst and/or an ethylene oxidation catalyst. In this general formula Z can be nothing or one or more of Nb, Sb, Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U and W, and (x) is equal to 0.5 to 0.9, (y) is equal to 0.1 to 0.4 and (z) is equal to 0 to 1. Many of these catalysts are known as shown by the prior art previously discussed and include compositions of the combinations of metals such as MoV, MoVNb, MoVSb, MoVNbSb, MoVCa, MoVNbSbCa, MoVNbSbSr, MoVNbSbMg, MoVNbSbFe, MoVNbSbCaK, and the like, shown without subscripts (x), (y) and (z).

The preferred molybdenum and vanadium calcined oxidation catalysts for use in the process of this invention are those of the formula $Mo_aV_bNb_cSb_dX_e$, wherein X is at least one of the metals Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U and W, preferably Ca; and (a) is equal to 0.5 to 0.9, (b) is equal to 0.1 to 0.4, (c) is equal to 0.001 to 0.2, (d) is equal to 0.001 to 0.1 and (e) is equal to 0.001 to 1.0. The values of (a), (b), (c), (d) and (e) constitute relative gram atoms of the respective elements in the catalyst. The elements are present in combination with oxygen in the form of various oxides. Illustrative of suitable ethylene hydration catalysts and ethylene oxidation catalysts are the molecular sieves, the palladium-containing catalysts, the tungsten-phosphorus-containing catalysts or the tin-molybdenum-containing catalysts.

DETAILED DESCRIPTION OF THE INVENTION

The catalytic oxydehydrogenation of ethane to ethylene as the major Product of the reaction and the oxidation of ethylene to produce acetic acid are known reactions. However, in the past selectivities have been less than desired and significant quantities of by-products have been produced. In fact, as previously shown, some of the prior art catalyst compositions have specifically noted the difficulties encountered with some catalysts in obtaining acetic acid.

In the process of this invention ethane, or ethylene, or a mixture of ethane and ethylene is catalytically oxidized in the vapor phase using a mixture of at least two different catalyst entities. The first catalyst entity is a calcined oxide oxidation catalyst composition of the formula:

$$Mo_xV_yZ_z \tag{I}$$

and preferably of the general formula:

$$Mo_aV_bNb_cSb_dX_e \tag{II}$$

as hereinbefore defined. Generally, this catalyst contains more than about 40 g atom percent molybdenum and more than about 2 g atom percent vanadium. The second catalyst entity includes one or more of the following classifications:
 (i) a molecular sieve catalyst such as a zeolite Y, or silicalite or an aluminophosphate or a metal aluminophosphate;
 (ii) a palladium-containing oxides catalyst;
 (iii) a tungsten-phosphorus-containing oxides catalyst;
 (iv) a tin-molybdenum-containing oxides catalyst.
These second catalyst entities are either ethylene hydration catalysts or ethylene oxidation catalysts.

The weight ratio of first catalyst entity to second catalyst entity can vary widely from about 20:1 to 1:20, preferably from 5:1 to 1:5. Any proportion can be used that is catalytically effective in the reaction. In general, the two entities are intimately premixed in dry form before charging the mixture to the reactor. Another procedure would be wet-mixing of the entities followed by drying and grinding. Any other suitable Procedure for combining the two entities can be used. One can also, if desired, have the separate entities present in the same reactor as separate alternating layers. Using the two entities in separate reactors, however, would not give the benefits achieved by this invention.

The process of this invention yields acetic acid at unexpected and unpredictable high selectivity and enables one to recycle ethylene formed as a by-product from the ethane charged to form the desired acetic acid. The catalysts can be used unsupported or supported.

The first catalyst entity

The first catalyst entity is well-known and many are fully described in U.S. Pat. No. 4,524,236, U.S. Pat. No. 4,250,346 and U.S. Pat. No. 4,568,790 previously mentioned. They have the compositions stated in the section entitled "Summary of the Invention", the preferred first catalyst entity being the calcined oxides composition $Mo_aV_bNb_cSb_dCa_e$.

Preferably, this catalyst entity is prepared from a solution of soluble compounds and/or complexes and/or compounds of each of the metals. The solution is preferably an aqueous system having a pH of 1 to 12 and more preferably a pH of 5±3, at a temperature of from about 20° C. to about 100° C.

Generally, a mixture of compounds containing the metal elements is prepared by dissolving sufficient quantities of soluble compounds of these metals and dispersing the insoluble compounds so as to provide the desired gram-atom ratios of the metal elements in the catalyst composition. The catalyst composition is then prepared by removing the water or other solvent from the mixture of the compounds in the solution system. The dried catalyst is calcined by heating to a temperature of from about 220° C. to about 550° C. in air or oxygen for a period of time from about one minute to about 24 hours to produce the desired catalyst composition. Generally, the higher the temperature the shorter the period of time required.

Suitable supports for this catalyst entity include silica, aluminum oxide, silicon carbide, zirconia, titania, and mixtures thereof. When used on a support, the supported catalyst usually comprises from about 10 to 50% by weight of the catalyst composition, with the remainder being the support.

Preferably, the molybdenum is introduced into the solution in the form of ammonium salts such as ammonium paramolybdate, or organic acid salts of molybdenum such as acetates, oxalates, mandelates, and glycolates. Some other partially water soluble molybdenum compound which may be used include molybdenum oxides, molybdic acid, and the chlorides of molybdenum.

Preferably, the vanadium is introduced into the solution in the form of ammonium salts such as ammonium meta-vanadate and ammonium decavanadate, or organic acid salts of vanadium such as acetates, oxalates, and tartrates. Partially water soluble vanadium compounds such as vanadium oxides, and sulfates of vanadium can be used.

Preferably, when it is present, the niobium is added in the form of the oxalate. Other sources of this metal in soluble form include compounds in which the metal is coordinated, bonded or complexed to a beta-diketonate, carboxylic acid, an amine, an alcohol, or an alkanolamine.

Preferably, when it is present, the antimony is introduced into solution in the form of antimony oxalate. Other soluble and insoluble compounds of antimony can be used such as antimony oxide and antimony chloride.

The Z or X component of the catalyst can be a soluble or insoluble compound preferably soluble. Compounds which are strongly reducing may adversely reduce the oxidation states of the metal.

The following are some preferable compounds for the Z or X component. One is calcium in the form of a water soluble chelate coordinated with ammonium lactate, and others are calcium compounds in which the metal is coordinated, or complexed to a beta-diketonate, a carboxylic acid, an amine, an alcohol or an alkanolamine. Generally, nitrates are desirable along with water soluble chlorides and organic acid salts such as acetates, oxalates, tartrates, lactates, salicylates, formates, and carbonates.

Preferably, this catalyst entity is prepared by the following general procedure. The vanadium compound is mixed with water to form a first solution or suspension, the niobium and antimony when used, are mixed with water to form a second solution or suspension, and molybdenum compound is mixed with water to form a third solution or suspension. Any Z or X compounds which are ammonium salts are mixed with the first solution. Otherwise, the Z or X compounds are mixed into the second solution. The first and second solutions are heated separately and mixed for about fifteen minutes; they are then combined and mixed with heating for about fifteen minutes. The third solution is heated and mixed, and then added to the combined first and second solutions to form a combined suspension or solution. After mixing and heating of the combined mixtures for about fifteen minutes the combined mixture is evaporated to dryness rapidly, in air usually, but the drying could be carried out in an inert atmosphere.

When this catalyst entity is to be used with a support, it is believed desirable to filter the combined solution to remove the insoluble portion before impregnating the support. The filtering can be carried out using sintered glass, or a paper filter with or without suction.

It has been found that catalyst surface area and activity depend on the digestion time, i.e., the time taken to evaporate the combined mixture to dryness. Compositions allowed to digest for relatively long periods of time, thirty minutes or more, before drying at 120° C. generally undergo particle growth with loss in surface area.

It is believed that this catalyst entity for the invention should have one or more of the metal components slightly below their highest possible oxidation states. The calcining is carried out with the flow of air or some other oxygen containing gas over the dry solids prepared from the solutions or suspensions to control the reducing actions of reducing agents such as $NH_3$ or organic reducing agents which are introduced into the solution system from which the catalysts are prepared. The rate of flow of the gas can be determined experimentally for the apparatus and the quantities of solids being used for optimizing the properties of the catalyst being produced.

One or more of the free valances of metals in the catalyst are occupied by one or more of oxide, hydroxyl, and $CO_3$.

In general, the catalyst, supported or unsupported, can be used in a fixed or fluidized bed.

The second catalyst entity

As previously indicated this is either an ethylene hydration catalyst or an ethylene oxidation catalyst, many of which are known.

The suitable ethylene hydration catalysts are those which will catalyze the reaction of ethylene present in the reactor with water to give ethanol or diethyl ether that will subsequently undergo further oxidation to acetic acid. Generally, these catalyst entities are acidic in nature. The solid ethylene hydration catalysts are preferred, though liquid hydration catalysts supported on the solid $Mo_xV_yZ_z$ or $Mo_aV_bNb_cSb_dX_e$ oxides catalyst component can also be used. Known olefin hydration catalyst entities include those of classifications (i) and (iii).

The suitable ethylene oxidation catalysts are those which catalyze the reaction of ethylene with oxygen to form oxygen-containing products, including acetic acid, acetaldehyde, glycols, other acids, etc. Generally, these catalyst entities are metal oxides, metal peroxides, or metals. Again solids are preferred, but liquid oxidation catalysts supported on the solid $Mo_xV_yZ_z$ or $Mo_aV_bNb_cSb_dX_e$ oxides catalyst component can also be used. Known olefin oxidation catalysts include those of classifications (ii) and (iv).

(i) The molecular sieve catalyst components are known as ethylene hydration catalysts, as reported in the Iwamoto et al article. However, it was not known that the combination of molecular sieves with the defined MoVZ or MoVNbSbX oxides compositions improves selectivity to acetic acid when oxidizing ethane, ethylene or mixtures of ethane and ethylene. This improved selectivity to acetic acid was completely unexpected and unpredictable. As shown by the data in the examples, higher selectivity to acetic acid is achieved using a combination of (A) the MoVZ or MoVNbSbX oxides catalyst plus (B) the molecular sieve catalyst than by use of either of these alone as the catalyst. This was observed whether the feed gas was ethane alone, ethylene alone, or a mixture of ethane plus ethylene. In addition, higher conversion of ethylene was achieved using the combination of the two catalyst entities as compared to use of each entity separately.

Typically molecular sieves are microporous inorganic oxide compounds having sites where ion exchange can occur. The molecular sieves useful in the process of this invention are those that are acidic in character and that catalyze the hydration of ethylene under the reaction conditions of the process of this invention. These materials are well-known to those of average skill in the art and many are commercially available. Illustrative are the zeolites, such as and zeolite Y, the high-silica zeolites such as LZ-105, ZSM-5, silicalite and, the aluminophosphate containing molecular sieves as described in E. M. Flanigen et al, "Aluminophosphate Molecular Sieves and the Periodic Table", 7th International Zeolite Conference, Tokyo, Aug. 17–22, 1986.

It is believed that those molecular sieves that are not acidic, for example sieves whose acidic sites have been essentially completely neutralized with base would not be expected to act as ethylene hydration catalysts. One skilled in the art is fully familiar with such distinctions and can readily select the proper molecular sieves.

(ii) The palladium-containing oxides catalyst components have been used in oxidation reactions, as shown in Japan 46-6763 and 54-57488; generally for the oxidation of ethylene. However, it has not been shown, to the best of our knowledge, that the combination of palladium-containing oxides catalysts with the defined MoVZ or MoVNbSbX oxides compositions improves selectivity to acetic acid when oxidizing ethane, ethylene or mixtures of ethane and ethylene. This improved selectivity to acetic acid was completely unexpected and unpredictable. As shown by the data in the examples, higher selectivity to acetic acid is achieved using a combination of (A) the MoVZ or the MoVNbSbX oxides catalyst plus (B) the palladium-containing oxides catalyst than by use of either of these alone as the catalyst. This was observed whether the feed gas was ethane alone, ethylene alone, or a mixture of ethane plus ethylene. Though palladium-containing oxides catalysts have been used as selective catalysts for conversion of ethylene to acetic acid, to the best of our knowledge they have not been disclosed as useful as selective catalysts for the conversion of ethane to acetic acid.

Any palladium-containing oxides catalyst that has a catalytic effect on the oxidation reaction can be used in combination with the MoVZ or MoVNbSbX oxides catalyst. The combination is believed to catalyze the reaction of ethane to ethylene and acetic acid; the ethylene formed further reacts, or is recycled, and acetic acid is produced with high selectivity. It was also noted that higher ethylene conversions were achieved when using the combination rather than a single entity as the catalyst.

While palladium-containing oxides compositions containing from 0.01% palladium to 99% palladium may be used, catalysts containing more than about 20% palladium become costly. Therefore, the generally preferred amount of palladium in the catalysts is from about 0.1% to about 10%, the balance being the other elements making up the catalyst entity and/or the support. The preparation of palladium-containing oxides catalyst compositions is well and fully documented in the literature and need not be fully described here. One of ordinary skill in the art, using the available technology and procedures, will have no difficulty in producing the palladium compositions.

Illustrated of suitable palladium-containing oxides compositions, unsupported or supported on a carrier (such as, alumina, silica, molecular sieve, or the like), are the oxides, oxide-sulfates, etc of Pd-V-Sb, or of Pd-V-P, or of Pd-Mo-Sb, or of Pd-Mo-As, or of Pd-Mo-P-W-Rh-Sb, or of Pd-Mo-P-V, as well as any other combination of one or more elements with Pd. One can also, if desired, use the catalyst on a suitable support. As previously noted, a large number of suitable palladium-containing oxides compositions are known, any of which can be used so long as they exert a catalytic effect on the process of this invention.

(iii) The tungsten-phosphorus-containing oxides catalysts are known as olefin hydration catalysts. As reported by Ai, he was unable to obtain acetic acid with catalysts of this type with a feed of butene; Ai has no data on feeds containing ethane or ethylene. To the best of our knowledge, tungsten-phosphorus-containing oxides are not known catalysts for oxidation of ethane, or ethylene, or mixtures of ethylene with ethane to acetic acid.

Tungsten-phosphorus-containing oxides provide when intermixed with MoVZ or MoVNbSbX oxides compositions a catalytic process that shows higher selectivity to acetic acid from ethylene alone, or ethane alone or mixtures of ethylene and ethane than does use of the tungsten-phosphorus oxides alone or of the MoVZ or MoVNbSbX oxides alone. This was unexpected and unpredictable because tungsten-phosphorus-containing oxides catalyst alone converts hardly any ethylene at all. Yet mixed with the MoVZ or the MoVNbSbX oxides catalyst, which by itself show only a low conversion of ethylene, the combinations greatly increase the conversion of ethylene and the selectivity to acetic acid.

The combination of MoVZ or MoVNbSbX oxides catalysts and the tungsten-phosphorus-containing oxides catalysts catalyzes the reaction to selectively produce acetic acid from ethane, ethylene, or mixtures of the two. While tungsten-phosphorus-containing oxides containing from about 0.01 g atom % to about 99.99 g atom % tungsten and from about 99.99 g atom % to about 0.01 g atom % phosphorus may be used, the compositions having more than about 50 g atom % tungsten are preferred. Most preferred are the catalysts containing about 80% tungsten and about 20% phosphorus. The mixed catalyst can be prepared by an intimate admixture, such admixture occurring by mixing the solids, or by mixing in solution, of any tungsten or phosphorus compounds that will form oxides under the reaction conditions or will form oxides by treatment, for example, by calcining at high temperature, prior to its introduction into the reactor. Particularly preferred as a source of tungsten is ammonium tungstate, though other tungsten compounds can be used. Particularly preferred as a source of phosphorus is phosphoric acid, though other phosphorus compounds can be used. The technology for preparation of the tungsten-phosphorus-containing oxides is readily available and well known to one of ordinary skill in the art.

(iv) Though the use of tin-molybdenum-containing oxides catalysts for the oxidation of olefins is known, as shown in the Tan et al article, supra, they are not known as selective oxidation catalysts for ethylene and Tan et al report that the product of the oxidation of ethylene over these catalysts was mainly carbon dioxide. It was therefore, completely unexpected and unpredictable that a combination of tin-molybdenum-containing oxide catalysts with MoVZ or MoVNbSbX oxides catalysts shows improved selectivity of ethylene, ethane or mixtures of ethane and ethylene to acetic acid. It was also surprising to find that we were able to obtain acetic acid from ethylene using the tin-molybdenum-containing oxide catalyst alone though at a lower selectivity than when the combination of oxides catalysts was used.

While tin-molybdenum-containing oxides containing from 0.01 g atom % to about 99.99 g atom % tin and from about 99.99 g atom % to about 0.01 g atom % molybdenum can be used, the compositions containing more than about 50 g atom % tin are preferred. Most preferred are the catalysts containing about 70% tin and about 30% molybdenum. The mixed catalyst can be prepared by intimate admixture, such admixture occurring by mixing the solids or by mixing in solution, of any tin and molybdenum compounds that will form oxides under the reaction conditions or will form oxides by treatment, for example, calcining at high temperature, prior to its introduction into the reactor. Particularly preferred as a source of tin is stannous chloride, though other tin salts can be used. Particularly preferred as a source of molybdenum is ammonium molybdate, though other molybdenum salts can be used. The technology for Preparation of tin-molybdenum-containing oxides is readily available and well known to one of ordinary skill in the art.

The reactor used in the Examples 1 to 22 was a stainless steel tubular reactor measuring 1.27 cm inside diameter and 20.3 cm long. The reactor is charged with the catalyst, supported or unsupported, and not necessarily completely filled with catalyst. It was immersed in a thermostated sand bath for temperature control purposes. The outlet was equipped with known means for recovery of gaseous and liquid products. Connected to the inlet of the reactor was a 20.3 cm. long by 0.7 cm. inside diameter stainless steel tube packed with glass beads, which served as a preheater. The preheater was heated by immersion in the same sand bath used for the reactor. Reactants were introduced into the preheater and from thence into the reactor with reactant flow monitored with a bubble meter at the end of the analytical train. Uncondensed product was passed through a water condenser and led through a condensation train of wet ice and then dry ice/acetone in series so that all low boiling product was recovered. Uncondensed gases and low boiling products were analyzed by standard gas chromatograph techniques.

The reaction mixture introduced into the reactor is generally in the ratio of one mole of hydrocarbon (ethane, ethylene) to 0.01 mole to 3 moles or more of oxygen either as pure oxygen or in the form of air, and zero to 4 moles or more of water in the form of steam. The water or steam is used as a reactant, a reaction diluent and heat moderator for the reaction.

The feed components are generally premixed prior to being introduced into the reaction zone. The reaction zone has a temperature of from about 75° C. to about 500° C., preferably from about 200° C. to about 400° C.

The pressure in the reactor can vary from about atmospheric pressure to about 75 atmospheres, preferably from 1 to about 30 atmospheres.

A contact time of from about 0.01 second to about 100 seconds, preferably from about 0.1 second to 10 seconds, of the reaction feed with the catalyst is maintained for the reaction. The contact time is defined as the ratio between the apparent volume of the catalyst bed and the volume of the gaseous reaction mixture feed to the catalyst bed under the given reaction conditions in a unit of time.

A space velocity in the reaction zone of from about 50 to 50,000 $h^{-1}$, preferably 100 to 10,000 $h^{-1}$ and most preferably 200 to 3,000 $h^{-1}$ is maintained. The space velocity is calculated by determining total reactor outlet gas equivalent in liters of the total effluent evolved over a period of one hour divided by the liters of catalyst in the reactor. This room temperature volume is converted to the volume at 0° C. at 760 mm Hg:

$$\text{space velocity} = \frac{\text{liters of outlet gas equivalents per hour}}{\text{liters of catalyst in reactor}} = h^{-1}$$

The oxygen concentration in the feed gas mixture can vary widely, from about 0.1 to about 50% oxygen or higher of the feed mixture. As previously indicated air is the preferred source of oxygen in the feed. The amount of oxygen present may be a stoichiometric amount, or higher, of the hydrocarbons in the feed, preferably, however, hydrocarbons will be in excess.

The process is generally carried out in a single stage with all of the oxygen and reactants being supplied as a single feed with unreacted initial reactants being recycled. However, multiple stage addition of oxygen to the reactor with intermediate hydrocarbon feed can also be used. The catalyst components should all be present in the same reactor for maximum benefits.

The amount of water or steam in the gaseous feed mixture will vary and about 10 weight percent to 30 weight percent in the feed is preferred.

In addition to the components referred to one can also have present in the feed small amounts of other compounds, e.g. ethanol, acetaldehyde.

It is believed when the second catalyst entity is a hydration catalyst it further catalyzes the hydration of ethylene either to ethanol or to diethyl ether that are then converted to acetic acid; when the second catalyst entity is an oxidation catalyst it catalyzes the reaction of ethylene to acetic acid and other oxidates that are then converted to acetic acid. The higher selectivity to acetic acid achieved by the processes of this invention was completely unexpected and unpredictable.

In a typical run, the temperature in the tubular reactor was lined out with nitrogen flow over the catalyst and then the gaseous reactants feed and water feed were started. After a suitable time at line-out conditions, which can vary at the whim and desire of the experimentor, the trap was drained and a timed run was begun. Gas analyses were conducted every 30 minutes. After, usually four hours, the trap was drained and nitrogen was turned into the reactor. Using methyl ethyl ketone as internal standard, the amount of acetic acid in the trap sample was determined. The average moles of oxygen and ethane and ethylene reacted and the average moles of acetic acid, ethylene and carbon oxides formed per minute were then calculated. Selectivities were calculated from these figures.

The following examples serve to further illustrate this invention.

EXAMPLE 1

(Run A) A $Mo_{0.7} V_{0.25} Nb_{0.02} Sb_{0.01} Ca_{0.01}$ calcined oxides catalyst was prepared by the procedure previously described using ammonium molybdate (4 g atoms of Mo), ammonium metavanadate (1.7 g atoms of V), niobium oxalate (0.47 g atom of Nb), antimony oxalate (0.25 g atom of Sb) and calcium nitrate (0.25 g atom of Ca). The compounds were thoroughly mixed in a total of 6,000 mL of water and filtered. The filtered solution was evaporated to dryness and the solids obtained broken to 20 to 40 mesh particles and then calcined in air at about 375° C. for five hours to give the catalyst.

The stainless steel tubular reactor was charged with the catalyst combination that was an intimate mixture of 4 grams of the unsupported $Mo_{0.7}V_{0.25}Nb_{0.02}Sb_{0.01}Ca_{0.01}$ calcined oxides catalyst, 2 grams of powdered molecular sieve LZ-105 catalyst (Union Carbide Corporation) and 4 cc of 20 to 30 mesh quartz chips. The reactor was heated in a sand bath thermostated at about 255° C. Water at a rate of 0.4 mL per hour was fed to a preheater connected to the reactor inlet; simultaneously a gas feed containing, by volume, 6.5% oxygen, 8% ethylene, 79% ethane and nitrogen was fed to the preheater at 60 mL per minute. The flow of gases from the preheater to the reactor was continued for 2.5 hours at a reactor temperature of 255° C. and a pressure of 100 psig and then it was arbitrarily stopped. Gaseous reaction effluent was analyzed for oxygen, nitrogen and carbon monoxide by gas chromatography at 65° C. using a 3 m by 3 mm column of 5A molecular sieve (60/80 mesh). Carbon dioxide, ethane and ethylene were analyzed using a 1.8 m by 0.3 mm column packed with material sold under the tradename POROPAK Q (50/80 mesh). The liquid products, acetic acid and water, were condensed in a cold-trap and were analyzed using a 3 m by 0.3 mm column packed with material sold under the tradename POROPAK R (60/80 mesh). In general, selectivity to acetic acid, ethylene and carbon oxides reported in the examples were calculated on a carbon-accounted for basis. During the ethylene-ethane oxidation the concentration of ethylene increased slightly, showing it was made a little faster than it reacted. Products of the reaction were acetic acid, ethylene and carbon oxides. Selectivity to acetic acid from ethane was 63 mole percent and to ethylene from ethane 14 mole percent. Conversion of ethane was 3 mole percent.

(Run B) For comparative purposes the process of Run A was repeated except only the MoVNbSbCa oxides catalyst component (4 grams) was charged to the reactor mixed together with the quartz chips. Selectivity to acetic acid from ethane was only 32 mole percent and selectivity to ethylene from ethane increased to 62 mole percent.

The data clearly establish the unexpected higher selectivity to acetic acid from ethane that is obtained in Run A with the combination of MoVNbSbCa oxides catalyst and molecular sieve catalyst when oxidizing a feed of mixed ethylene and ethane as compared to Run B results. The selectivity to acetic acid was twice as high, 63 vs. 32 mole percent.

EXAMPLE 2

(Run A) Using the same catalyst combination, apparatus and procedure described in Example 1, the oxidation of ethylene alone was carried out. In addition to the water vapor (steam), the gas feed introduced into the reactor was made up of 6.5% oxygen, 8% ethylene, 6.5% nitrogen and 79% helium. The products of the ethylene oxidation reaction were acetic acid and carbon oxides. The selectivity to acetic acid from ethylene was 74 mole percent. Conversion of ethylene was 31 mole percent.

(Run B) For comparative purposes the process of Run A was repeated except only the MoVNbSbCa oxides catalyst component (4 g) mixed with quartz chips was charged to the reactor. Again the products of the reaction were acetic acid and carbon oxides. However, the selectivity to acetic acid from ethylene dropped to a low value of 41 mole percent, only about one-half of the selectivity obtained in Run A. Conversion of ethylene dropped to the low value of only 5 mole percent.

(Run C) For further comparative purposes the process of Run A was again repeated except only the molecular sieve LZ-105 catalyst component (2 g intimately mixed with 12 g of the quartz chips) was charged to the reactor. Again the products of the reaction were acetic acid and carbon oxides. However, selectivity to acetic acid from ethylene dropped to the low value of 21 mole percent, only about 28% of the selectivity obtained in Run A. Conversion of ethylene dropped to the extremely low value of only 2 mole percent.

The data clearly establish the unexpected higher selectivity and conversion achieved from the oxidation of ethylene with the catalysts combination of MoVNbSbCa oxides catalyst and molecular sieve catalyst in Run A as compared to the oxidation using only one of these materials as the sole catalyst component in Runs B and C.

EXAMPLE 3

The apparatus and procedure used in Example 2 were followed. The same catalyst composition was used except that the molecular sieve catalyst component was SAPO-34 (U.S. Pat. No. 4,440,871). The products of the ethylene oxidation reaction were acetic acid and carbon oxides. Selectivity to acetic acid from ethylene was 48 mole percent. Conversion of ethylene was 9 mole percent.

EXAMPLE 4

The apparatus and procedure used in Example 2 were followed. The same catalyst composition was used except that the molecular sieve catalyst component was the commercially available AW-500 (Union Carbide Corporation). The products of the ethylene oxidation reaction were acetic acid and carbon oxides. Selectivity to acetic acid from ethylene was 56 mole percent. Conversion of ethylene was 7 mole percent.

EXAMPLE 5

The apparatus and procedure used in Example 2 were followed. The same catalyst composition was used except that the molecular sieve catalyst component was Zeolon 700 (Norton Chemical Process Products). The products of the ethylene oxidation reaction were acetic acid and carbon oxides. Selectivity to acetic acid from ethylene was 58 mole percent. Conversion of ethylene was 7 mole percent.

EXAMPLE 6

The apparatus and procedure used in Example 2 were followed. The same catalyst composition was used except that the molecular sieve catalyst component was SAPO-11 (U.S. Pat. No. 4,440,871). The products of the ethylene oxidation reaction were acetic acid and carbon oxides. Selectivity to acetic acid from ethylene was 64 mole percent. Conversion of ethylene was 4 mole percent.

EXAMPLE 7

(Run A) Using the same catalyst combination, apparatus and procedure described in Example 1, the oxidation of ethane alone was carried out. In addition to the water vapor (steam), the gas feed introduced into the reactor was made up of 87% ethane 6.5% oxygen and 6.5% nitrogen. The products of the ethane oxidation reaction were acetic acid, ethylene and carbon oxides. The selectivity to acetic acid from ethane was 39 mole percent; the selectivity to ethylene from ethane was 56 mole percent. Conversion of ethane was 3 mole percent.

(Run B) For comparative purposes the process of Run A was repeated except only the MoVNbSbCa oxides catalyst component (6.1 grams) was charged to the reactor mixed together with the quartz chips. The products of the reaction were acetic acid, ethylene and carbon oxides. The selectivity to acetic acid from ethane was 28 mole percent; the selectivity to ethylene from ethane was 65 mole percent. Conversion of ethane was 7 mole percent.

The data show the higher selectivity to acetic acid from ethane achieved in Run A using the catalysts combination of this invention as compared to using the single component catalyst in Run B.

EXAMPLE 8

(Run A) A $Pd_{0.04} V_{0.68} Sb_{0.28}$ oxides-sulfate palladium-containing catalyst was prepared by the procedure described in Example 6 in Japan 46-6763 using ammonium metavanadate (10.5 g), palladium chloride (1.5 g) and antimony sulfate (10 g). The three salts were dissolved in 100 mL of hot concentrated hydrochloric acid and then 60 mL of alpha alumina (20–40 mesh) were added with stirring. The liquid was evaporated using a rotary evaporator, the residual solid was dried overnight at about 110° C., crushed to 20 to 40 mesh and calcined in a flow of air for 4 hours at 450° C.

The stainless steel tubular reactor described in Example 1 was charged with an intimate mixture of 4 g of the MoVNbSbCa calcined oxide catalyst described in Example 1, 2 g of the PdVSb oxides-sulfate palladium-containing catalyst prepared above and 4 cc of 20 to 30 mesh quartz chips. Following the procedure described in Example 1, the same ethylene-ethane-containing gaseous feed mixture described in Example 1 was oxidized. The gaseous and liquid products of the reaction were analyzed as described therein. During the ethylene-ethane oxidation reaction, the concentration of ethylene decreased slightly, indicating it reacted faster than it was made. The selectivity to acetic acid from ethane was 77 mole percent. Conversion of ethane was 3 mole percent.

(Run B) For comparative purposes the process of Run A was repeated except only the MoVNbSbCa oxides catalyst component (4 grams) mixed with the quartz chips was charged to the reactor. In this Run B, the concentration of ethylene increased slightly during the reaction, showing it was made faster than it reacted. Ethylene, on net, was made in the reactor, and less acetic acid was produced. The selectivity to acetic and from ethane was 32 mole percent; the selectivity to ethylene from ethane was 62 mole percent. Conversion of ethane was 3 mole percent. This control is the same as Example 1 (Run B).

The data show an unexpected selectivity to acetic acid from ethane in Run A using the combination of MoVNbSbCa oxides catalyst and the palladium-containing catalyst that is more than twice the selectivity obtained with the MoVNbSbCa oxides catalyst alone in Run 8 when oxidizing a feed of mixed ethylene and ethane.

EXAMPLE 9-1

(Run A) A $Na_{0.06} Pd_{0.03} H_{0.11} P_{0.07} Mo_{0.68} V_{0.06}$ oxides catalyst was prepared by the procedure described in Example 1 in Japan 54-57488. Phosphomolybdic acid (11.9 g) was dissolved in 100 mL of hot water and then, sequentially sodium metavanadate (0.6 g) in 100 mL of water and palladium acetate (0.5 g) in 50 mL of acetone were added with stirring. The liquid was evaporated using a rotary evaporator, the residual solid was dried overnight at 110° C., crushed to 20 to 40 mesh and calcined in a flow of air for 5 hours at 320° C.

The stainless steel tubular reactor described in Example 1 was charged with an intimate mixture of 4 grams of the MoVNbSbCa oxides catalyst described in Example 1, 2 grams of the NaPdHPMoV oxides palladium-containing catalyst prepared above and 4 cc of 20 to 30 mesh quartz chips. Following the procedure described in Example 2, the same ethylene-containing gaseous feed mixture described in Example 2 was oxidized. The gaseous and liquid products of the reaction were analyzed as described in Example 1. The products of the ethylene oxidation reaction were acetic acid and carbon oxides. Selectivity to acetic acid from ethylene was 55 mole percent. The conversion of ethylene was 34 mole percent.

(Run B) For comparative purposes the process of Run A was repeated except only the NaPdHPMoV oxides palladium-containing catalyst component (2 grams) mixed with 12 cc of quartz chips was charged to the reactor. The products of the ethylene oxidation reaction were acetic acid and carbon oxides. Selectivity to acetic acid from ethylene was 52 mole percent. The conversion of ethylene was 9 mole percent.

The 34 mole percent conversion of ethylene over the mixture attained in Run A versus the 9 mole percent conversion of ethylene over the single palladium-containing catalyst component attained in Run B was completely unexpected.

A comparison of the ethylene to acetic acid selectivity of 55 mole percent and conversion of 34 mole percent achieved in Run A using the mixture of two catalyst components as the oxidation catalyst with the ethylene to acetic acid selectivity of 47 mole percent and conversion of 5 mole percent in comparative Run B of Example 2 in which only the MoVNbSbCa oxides catalyst component was used as the oxidation catalyst shows the unexpected higher selectivities and conversions achieved using the combination of MoVNbSbCa oxides catalyst and the palladium-containing catalyst component as the oxidation catalyst in the same reactor.

EXAMPLE 9-2

The tubular reactor was charged with an intimate mixture of the MoVNbSbCa oxides catalyst (4 grams) described in Example 1, the NaPdHPMoV oxides palladium-containing catalyst (2 grams) described in Example 9-1 and 4 cc of the quartz chips. Following the procedure described in Example 1, the same ethane-ethylene-containing gaseous feed mixture described in Example 1 was oxidized. The gaseous and liquid products of the reaction were analyzed as described in Example 1. The products of the ethane-ethylene oxidation reaction were acetic acid and carbon oxides. Selectivity to acetic acid from ethane was 73 mole percent and to ethylene from ethane zero mole percent. The conversion of ethane was 3 mole percent.

EXAMPLE 10

(Run A) The tubular reactor was charged with an intimate mixture of the MoVNbSbCa oxides catalyst (4 grams) described in Example 1, the PdVSb oxides-sulfate catalyst (2 grams) described in Example 8 and 4 cc of quartz chips. Following the procedure described in Example 2, the same ethylene-containing gaseous feed mixture described in Example 2 was oxidized. The gaseous and liquid products of the reaction were analyzed as described in Example 1. The products of the ethylene oxidation reaction were acetic acid and carbon oxides. Selectivity to acetic acid from ethylene was 54 mole percent. The conversion of ethylene was 33 mole percent.

(Run 8) For comparative purposes the process of Run A was repeated except only the PdVSb oxides-sulfate catalyst component (2 grams) mixed with 12 cc of quartz chips was charged to the reactor. The products of the ethylene oxidation reaction were acetic acid and carbon oxides. The selectivity to acetic acid from ethylene was 43 mole percent. The conversion of ethylene was 26 mole percent.

The data show the higher conversion of ethylene and the higher selectivity to acetic acid from ethylene achieved using the combination of MoVNbSbCa oxides catalyst and palladium-containing catalyst (Run A) of this invention as compared to use of the single palladium-containing catalyst (Run B).

Again, comparison of the selectivity and conversion results of Run A of this example using the mixture of two catalyst components as the oxidation catalyst with the values reported for comparative Run B of Example 2 in which only the MoVNbSbCa oxides catalyst component shows the unexpected higher selectivities and conversions achieved using the catalysts mixtures of this invention.

EXAMPLE 11

A $W_{0.8} P_{0.2}$ oxides catalyst was prepared by the procedure described by Ai (J. Catal. 49, 313 (1977)). To ammonium metatungstate (25 grams) in 200 mL of distilled water there was added at 80° C. 2.9 grams of 85% phosphoric acid followed by 1.2 g of oxalic acid. After stirring at 80° C. for two hours, the mixture was evaporated to dryness in a steam dish. The residue was ground and sieved (20–40 mesh) and calcined in a flow of air for 5 hours at 500° C.

The stainless steel tubular reactor described in Example 1 was charged with an intimate mixture of 4 grams of the MoVNbSbCa oxides catalyst described in Example 1, 2 grams of the WP oxides catalyst prepared above and 2 cc of quartz chips (20–30 mesh). Following the procedure described in Example 1, the same ethylene-ethane-containing gaseous feed mixture described in Example 1 was oxidized. The products formed during the reaction were acetic acid, ethylene and carbon oxides; during the reaction ethane and oxygen, in net reacted. The products were analyzed as described in Example 1. The selectivity to acetic acid from ethane was 77 mole percent; the selectivity to ethylene from ethane was 2 mole percent. The conversion of ethane was 2.1 mole percent.

The unexpected higher selectivity obtained by the mixed MoVNbSbCa oxides catalyst plus the WP oxides catalyst in this example is apparent when the results are compared to those of Example 1 (Run B) in which the sole catalyst component was the MoVNbSbCa oxides catalyst and to those of Example 15 (Run B) in which the sole catalyst component was the WP oxides catalyst. In this example selectivity to acetic acid was 77%, in Example 1 (Run B) selectivity to acetic acid was only 32%, and in Example 15 (Run B) no acetic acid formed (a selectivity of zero percent). Thus, it is apparent that the combination of this invention yields unexpected and unpredictable results.

EXAMPLE 12

The apparatus and procedures used in Example 11 were followed. In this example the $W_{0.8} P_{0.2}$ oxides catalyst used was made without oxalic acid added during its preparation. The tubular reactor was charged with an intimate mixture of the MoVNbSbCa oxides catalyst (4 grams) described in Example 1, the WP oxides catalyst prepared as described here (2 grams) and the quartz chips. All of the other reaction conditions were similar to those described in Example 11. The products of the ethane-ethylene mixture oxidation reaction were acetic acid, ethylene and carbon oxides. The selectivity to acetic acid from ethane was 50 mole percent; the selectivity to ethylene from ethane was 27 mole percent. Conversion of ethane was 2 Percent. Making the same comparisons made in Example 11 one again sees the higher selectivities obtained with this invention.

EXAMPLE 13

The apparatus and procedures used in Example 11 were followed. In this example a $W_{0.38} P_{0.09} Cr_{0.53}$ oxides catalyst was used with the MoVNbSbCa oxides catalyst (4 grams) component. This WPCr oxides catalyst component (2 grams) was made with oxalic acid and with the addition of 5.6 grams of chromic nitrate to the mixture before stirring and evaporation. The products of the ethane-ethylene oxidation reaction were acetic acid, ethylene and carbon oxides. The selectivity to acetic acid from ethane was 42 mole percent; the selectivity to ethylene from ethane was 46 mole percent. Conversion of ethane was 4 mole percent.

EXAMPLE 14

The apparatus and procedure used in Example 11 were followed. In this example, the $W_{0.38} P_{0.09} Cr_{0.53}$ mixed oxides catalyst was prepared as described in Example 13 but without the use of oxalic acid. The tubular reactor was charged with the MoVNbSbCa oxides catalyst (4 grams) of Example 1, the WPCr oxides catalyst (2 grams) and the quartz chips. The products of the ethane-ethylene mixture oxidation reaction were acetic acid, ethylene and carbon oxides. The selectivity to acetic acid from ethane was 40 mole percent; the selectivity to ethylene from ethane was 49 mole percent. Conversion of ethane was 3.4 mole percent. Making the same comparisons made in Example 11 one again sees the higher selectivities obtained in this invention.

EXAMPLE 15

(Run A) The tubular reactor was charged with an intimate mixture of the MoVNbSbCa oxides catalyst (4 grams) described in Example 1, the WP oxides catalyst (2 grams) described in Example 11 and 4 cc of quartz chips. Following the procedure described in Example 2, the same ethylene-containing gaseous feed mixture described in Example 2 was oxidized. The gaseous and liquid products of the reaction were analyzed as described in Example 1. The products of the ethylene oxidation reaction were acetic acid and carbon oxides. Selectivity to acetic acid from ethylene was 74 mole percent. The conversion of ethylene was 20 mole percent.

(Run B) For comparative purposes the process of Run A was repeated except only the WP oxides catalyst component (2 grams) mixed with 12 cc of quartz chips was charged to the reactor. Very little reaction occurred and no detectable acetic acid was produced.

The data show the unexpected high selectivity to acetic from ethylene obtained when using the combination of MoVNbSbCa oxides catalyst component plus WP oxides component in Run A of Example 15 as compared to the use of MoVNbSbCa oxides catalyst alone in Run B of Example 2 and as compared to WP oxides catalyst alone in Run B of Example 15.

EXAMPLE 16

The tubular reactor was charged with an intimate mixture of the MoVNbSbCa oxides catalyst (4 grams) described in Example 1, the WPCr oxides catalyst (2 grams) described in Example 13 and 4 cc of quartz chips. Following the procedure described in Example 2, the ethylene-containing gaseous feed mixture described in Example 2 was oxidized. The gaseous and liquid products of the reaction were analyzed as described in Example 1. The products of the ethylene oxidation reaction were acetic acid and carbon oxides. Selectivity to acetic acid from ethylene was 57 mole percent. The conversion of ethylene was 13 mole percent.

EXAMPLE 17

The tubular reactor was charged with an intimate mixture of the MoVNbSbCa oxides catalyst (4 grams) described in Example 1, the WP oxides catalyst (2 grams) described in Example 12 and 4 cc of quartz chips. Following the procedure described in Example 2, the ethylene-containing gaseous feed mixture described in Example 2 was oxidized. The gaseous and liquid products of the reaction were analyzed as described in Example 1. The products of the ethylene oxidation reaction were acetic acid and carbon oxides. Selectivity to acetic acid from ethylene was 29 mole percent. The conversion of ethylene was 12 mole percent.

EXAMPLE 18

The tubular reactor was charged with an intimate mixture of the MoVNbSbCa oxides catalyst (4 grams) described in Example 1, the WPCr oxides catalyst (2 grams) described in Example 14 and 4 cc of quartz chips. Following the procedure described in Example 18. The ethylene-containing gaseous feed mixture described in Example 2 was oxidized. The gaseous and liquid products of the reaction were analyzed as described in Example 1. The products of the ethylene oxidation reaction were acetic acid and carbon oxides. Selectivity to acetic acid from ethylene was 59 mole percent. The conversion of ethylene was 12 mole percent.

EXAMPLE 19

The $Sn_{0.7}Mo_{0.3}$ oxides catalyst was prepared by the procedure described by Ai (J. Catal., 49, 313 (1977)). To stannous chloride dihydrate (210.5 grams) in 2,000 mL of water at 70° C. was added 3% aqueous ammonia until precipitation stopped. The solids were washed until chloride-free, slurried in water and the slurry was added with stirring at 80° C. to ammonium molybdate tetrahydrate (70.6 grams) dissolved in a minimum of water. The resulting mixture was evaporated to dryness in a steam dish, the solids were sieved to 20 to 40 mesh, dried overnight at 120° C. and then calcined in a flow of air for 5 hours at 500° C.

The stainless steel tubular reactor was charged with an intimate mixture of the MoVNbSbCa oxides catalyst (4 grams) described in Example 1, 2 grams of the SnMo oxides catalyst prepared above and 2 cc of the quartz chips. Following the procedure described in Example 1, except that the reactor pressure was 165 psig and the sand bath was thermostated at 306° C., a gaseous feed containing the water vapor and a gas feed containing 6.7% oxygen, 70% ethane, 7% ethylene and 16.7% helium was oxidized. During reaction the concentration of ethylene did not change, showing it reacted as quickly as it was made. Ethane and oxygen, in net, reacted and the products formed were acetic acid and carbon oxides. The selectivity to acetic acid from ethane was 78 mole percent. The conversion of ethane was 3 mole percent.

Comparison with Run B of Example 1 shows the unpredictably higher selectivity to acetic acid from ethane attained using the combination of MoVNbSbCa oxides plus SnMo oxides catalysts versus use of only MoVNbSbCa oxides catalyst, 78% vs 32%, respectively.

EXAMPLE 20

(Run A) The tubular reactor was charged with the same catalysts mixture described in Example 19. The sand bath was thermostated at 255° C. and the reactor pressure was 100 psig. Following the procedure described in Example 1, the ethane-ethylene-containing gaseous feed mixture described in Example 1 was oxidized. The gaseous and liquid products of this reaction were analyzed as described in Example 1. Ethane was consumed, but ethylene, in net, was neither made nor consumed in the reactor. The products of the reaction were acetic acid and carbon oxides. The selectivity to acetic acid from ethane was 83 mole percent with the selectivity to ethylene from ethane being zero. The conversion of ethane was 4 mole percent.

(Run B) For comparative purposes the process of Run A was repeated except only the SnMo oxides catalyst component (2 grams) mixed with 12 cc of quartz chips was charged to the reactor. Ethylene, in net, was consumed in the reaction but there was no apparent reaction of ethane. The products of the reaction were acetic acid and carbon oxides. The selectivity to acetic acid from ethylene was 37 mole percent with the selectivity to acetic acid and/or ethylene from ethane being zero. The conversion of ethylene was 3 mole percent.

The data show the unexpected and unpredictable higher selectivity to acetic acid achieved in Run A of Example 20 when using the combination of MoVNbSbCa oxides catalyst plus the SnMo oxides catalyst vs. the selectivity achieved in Run B of Example 1 when using only the MoVNbSbCa oxides catalyst, 83% vs 32%, respectively. The data also show the unexpected and unpredictable higher selectivity to acetic acid achieved when using said combination (Example 20, Run A) vs. the selectivity achieved when using only the SnMo oxides catalyst (Example 20, Run B), 83% vs 37%, respectively.

EXAMPLE 21

(Run A) The tubular reactor was charged with an intimate mixture of the MoVNbSbCa oxides catalyst (4 grams) described in Example 1, the SnMo oxides catalyst (2 grams) described in Example 19 and 4 cc of the quartz chips. Following the procedure described in Example 2, the ethylene-containing gaseous feed mixture described in Example 2 was oxidized. The gaseous and liquid products of the reaction were analyzed as described in Example 1. The products of the ethylene oxidation reaction were acetic acid and carbon oxides. The selectivity to acetic acid from ethylene was 65 mole percent. The conversion of ethylene was 34 mole percent.

(Run B) For comparative purposes the process of Run A was repeated except only the SnMo oxides catalyst component (2 grams) mixed with 12 cc of quartz chips was charged to the reactor. The products of the ethylene oxidation reaction were acetic acid and carbon oxides. The selectivity to acetic acid from ethylene was 26 mole percent. The conversion of ethylene was 32 mole percent.

The data clearly show the unexpected and unpredicted higher selectivity to acetic acid achieved using the combination of MoVNbSbCa oxides plus the SnMo oxides catalysts mixture, 65% (Run A), vs. the use of the SnMo oxides catalyst alone, 26% (Run B). A comparison of the selectivity of Run A of Example 21, which uses the combination catalyst mixture of this invention, with the selectivity of Run B of Example 2, which uses only the MoVNbSbCa oxides catalyst, also show the higher selectivity achieved by this invention, 65% vs 47%, respectively.

EXAMPLE 22

The tubular reactor was charged with the same catalysts mixture described in Example 21, Run A. Following the procedure described in Example 1, the ethane-containing gaseous feed mixture described in Example 7 was oxidized. The gaseous and liquid reaction products were analyzed as described in Example 1. The products of the reaction were acetic acid, ethylene and carbon oxides. The selectivity to acetic acid from ethane was 34 mole percent; the selectivity to ethylene from ethane was 62 mole percent. The conversion of ethane was 4 mole percent.

Comparison of the 34% selectivity to acetic acid from ethane reported above with the 28% selectivity reported in Example 7, Run 8, with the use of the MoVNbSbCa oxides catalyst alone, shows the higher selectivity achieved in Example 22.

EXAMPLE 23

(Run A) A $Mo_{0.69}V_{0.25}Nb_{0.06}$ calcined oxides catalyst was prepared by the following procedure. Ammonium metavanadate (0.145 g atom of V) was dissolved in 200 mL of distilled water and stirred for 15 minutes at 70° C. Niobium oxalate (0.035 g atom of Nb) was stirred in another 200 mL of 70° C. water for 15 minutes and then added to the vanadium-containing solution and the whole was stirred at 70° C. for 15 minutes. Ammonium molybdate (0.4 g atom of Mo) was dissolved in 200 mL of 70° C. water and added to the prior mixture. The whole mixture was stirred for 15 minutes at 70° C. and then evaporated to dryness as rapidly as possible in a stainless steel steam-heated evaporating dish. The resulting solids were ground and sieved to 20 to 40 mesh, dried overnight at 120° C. and calcined in air at 350° C. for 5 hours.

A stainless steel tubular reactor measuring 1.27 cm inside diameter and 12.7 cm long was charged with the catalyst combination that was an intimate mixture of 4 grams of the MoVNb calcined oxides catalyst prepared above, 2 grams of a $Sn_7Mo_{0.3}$ oxides catalyst prepared as described in Example 19, and 3 cc of 20 to 40 mesh quartz chips. Following the procedure and conditions used in Example 2, ethylene was oxidized to acetic acid at a reaction temperature of 256° C.; after three hours the reaction was arbitrarily terminated. The gas feed introduced into the reactor was made up of 8% ethylene, 6.5% oxygen, 6.5% nitrogen and 79% helium. Water vapor was also present. The products of the ethylene oxidation reaction were acetic acid and carbon oxides. The selectivity to acetic acid from ethylene was 64 mole percent. Conversion of ethylene was 36 mol percent.

(Run B) For comparative purposes the process of Run A was repeated except only the MoVNb oxides catalyst component (4 grams) mixed with quartz chips was charged to the reactor and the reaction was carried out for 2.5 hours. Again the products of the reaction were acetic acid and carbon oxides. The selectivity to acetic acid from ethylene was 67 mole percent, but the conversion of ethylene to acetic acid dropped to 16 mole percent.

EXAMPLE 24

(Run A) Using the same catalyst combination, apparatus and procedure described in Example 23, the oxidation of a mixture of ethylene and ethane was carried out. In addition to the water vapor (steam), the gas feed introduced into the reactor was made up of 79% ethane, 8% ethylene, 6.5% oxygen and 6.5% nitrogen. The reaction was arbitrarily terminated after 2.75 hours and the products of the reaction were acetic acid and carbon oxides. Ethylene and ethane both reacted; the conversion of ethylene was 15 mole percent and the conversion of ethane was 3 mole percent. The selectivity to acetic acid from ethane plus ethylene was 82 mole percent.

(Run B) For comparative purposes the process of Run A was repeated except only the MoVNb oxides catalyst component (4 grams) mixed with quartz chips was charged to the reactor and the reaction was carried out for 2.5 hours. Ethylene, on net, was produced during the reaction. The conversion of ethane was 4 mole percent. The selectivity to ethylene from ethane was 40 mole percent and the selectivity to acetic acid from ethane was 49 mole percent.

The data shows the unexpected and unpredictable higher selectivity to acetic acid obtained in Run A by the use of the combination of MoVNb oxides catalyst and SnMo oxides catalyst over the selectivity to acetic acid obtained in Run B using only the MoVNb oxides catalyst.

EXAMPLE 25

(Run A) A $Mo_{0.82}V_{0.18}$ oxides on silica catalyst was prepared by the following procedure. Ammonium metavanadate (0.044g atom of V) was dissolved in 100 mL of distilled water at 70° C. and stirred 15 minutes. Ammonium molybdate (0.2 g atom of Mo) was dissolved in 100 mL of distilled water, stirred for 15 minutes, added to the vanadium-containing solution, and the whole was stirred for 15 minutes at 70° C. Silica gel (34 g of Cab-O-

Sil M-5) and 50 mL of distilled water were added with stirring and then the resulting mixture was evaporated to dryness as rapidly as possible in a stainless steel steam-heated evaporating dish. The resulting solids were sieved, dried overnight at 120° C., and calcined in air at 350° C. for 5 hours.

Using the same apparatus and procedure described in Example 23, the reactor was charged with a catalyst combination that was an intimate mixture of 4 grams of the MoV calcined oxides on silica catalyst prepared above and 2 grams of a $Sn_{0.7}Mo_{0.3}$ oxides catalyst prepared as described in Example 19. The gas feed was the same as described in Example 23 and the reaction was arbitrarily stopped after 2.5 hours. The products of the reaction were acetic acid and carbon oxides. The selectivity to acetic acid from ethylene was 64 mole percent. Conversion of ethylene was 42 mole percent.

(Run B) For comparative purposes the process of Run A was repeated except only the MoV calcined oxides on silica component (4 grams) was charged to the reaction and the reaction was carried out for 3.5 hours. The products of the reaction were acetic acid and carbon oxides. Though the selectivity to acetic acid from ethylene was 63 mole percent, the conversion of ethylene was only 14 mole percent. This shows the unexpected and unpredictable improvement achieved with the process of this invention.

EXAMPLE 26

(Run A) Using the same catalyst combination, apparatus and procedure described in Example 25 the oxidation of a mixture of ethylene and ethane was carried out. In addition to the water vapor (steam) the gas feed introduced into the reactor was made up of 79% ethane, 8% ethylene, 6.5% oxygen and 6.5% nitrogen. The reaction was arbitrarily terminated after 3 hours and the products of the reaction were acetic acid and carbon oxides. Ethylene and ethane both, on net, reacted; the conversion of ethylene was 30 mole percent; the conversion of ethane was 0.4 mole percent; and the total conversion of ethane plus ethylene was 3 mole percent. The selectivity to acetic acid from ethane plus ethylene was 65 mole percent.

(Run B) For comparative purposes the process of Run A was repeated except only the MoV calcined oxides on silica component (4 grams) was charged to the reactor. The products of the reaction were acetic acid and carbon oxides. In this run ethylene, on net, was neither produced or consumed. The conversion of ethane was one mole percent and the selectivity to acetic acid from ethane was 62 mole percent.

What is claimed is:

1. A process for the selective production of acetic acid from a gaseous feed of ethane, ethylene, or mixtures thereof, and oxygen at a temperature of from about 75° C. to about 500° C. and a pressure of from about one atmosphere to about 75 atmospheres in the gaseous phase which comprises contacting said gaseous feed with a catalyst mixture containing component (A) and component (B) wherein:

component (A) is at least one calcined catalyst represented by the formula: $Mo_xV_yZ_z$ in the form of its mixed oxides, wherein
(x) is equal to 0.5 to 0.9;
(y) is equal to 0.1 to 0.4;
(z) is equal to 0 to 1; and
Z, when present, is one or more of the metals Nb, Sb, Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U and W;

and component (B) is at least one catalyst selected from the group consisting of
(i) a molecular sieve catalyst having acidic character;
(ii) a palladium-containing oxides catalyst;
(iii) a tungsten-phosphorus-containing oxides catalyst; or
(iv) a tin-molybdenum-containing oxides catalyst.

2. A process as claimed in claim 1, wherein (z) is 0 and said component (a) is represented by the formula:

$Mo_xV_y$

3. A process as claimed in claim 1, wherein said component (a) is represented by the formula:

$Mo_xV_yNb_z$ wherein (z) is 0.001–1.

4. A process as claimed in claim 1, wherein said component (a) is represented by the formula:

$Mo_xV_ySb_z$ wherein (z) is 0.001–1.

5. A process as claimed in claim 1, wherein said component (a) is represented by the formula:

$Mo_xV_y(NbSb)_z$ wherein (z) is 0.001–1.

6. A process as claimed in claim 1, wherein said component (a) is represented by the formula:

$Mo_aV_bNb_cSb_dX_e$ in the form of its mixed oxides, wherein
X is at least one of the metals Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U and W;
(a) is equal to 0.5 to 0.9;
(b) is equal to 0.1 to 0.4;
(c) is equal to 0.001 to 0.2;
(d) is equal to 0.001 to 1; and
(e) is equal to 0.001 to 1.

7. A process as claimed in claim 6, wherein component (A) is $Mo_aV_bNb_cSb_dCa_e$ mixed oxides wherein (a), (b), (c), (d) and (e) are as defined in claim 6.

8. A process as claimed in claim 1, wherein said gaseous feed comprises ethane, ethylene and oxygen.

9. A process as claimed in claim 6, wherein said gaseous feed comprises ethane, ethylene and oxygen.

10. A process as claimed in claim 1, wherein said gaseous feed comprises ethylene and oxygen.

11. A process as claimed in claim 6, wherein said gaseous feed comprises ethylene and oxygen.

12. A process as claimed in claim 1, wherein said gaseous feed comprises ethane and oxygen.

13. A process as claimed in claim 6, wherein said gaseous feed comprises ethane and oxygen.

14. A process as claimed in claim 7, wherein said gaseous feed comprises ethane, ethylene and oxygen.

15. A process as claimed in claim 7, wherein said gaseous feed comprises, ethylene and oxygen.

16. A process as claimed in claim 7, wherein said gaseous feed comprises ethane and oxygen.

17. A process as claimed in claim 1, wherein component (A) is:

$$Mo_xV_yZ_z$$

wherein Z, (x), (y) and (z) are as defined in claim 1 and component (B) is a molecular sieve catalyst.

18. A process as claimed in claim 6, wherein component (A) is $Mo_aV_bNb_cSb_dX_e$ mixed oxides wherein X, (a), (b), (c), (d) and (e) are as defined in claim 6 and component (B) is a molecular sieve catalyst.

19. A process as claimed in claim 6, wherein component (A) is $$Mo_aV_bNb_cSb_dCa_e$$

mixed oxides wherein (a), (b), (c), (d) and (e) are as defined in claim 6 and component (B) is a molecular sieve catalyst.

20. A process as claimed in claim 19, wherein said gaseous feed comprises ethane, ethylene and oxygen.

21. A process as claimed in claim 19, wherein said gaseous feed comprises ethylene and oxygen.

22. A process as claimed in claim 19, wherein said gaseous feed comprises ethane and oxygen.

23. A process as claimed in claim 20, wherein the molecular sieve catalyst component (B) is LZ-105.

24. A process as claimed in claim 21, wherein the molecular sieve catalyst component (B) is LZ-105.

25. A process as claimed in claim 21, wherein the molecular sieve catalyst component (B) is SAPO-34.

26. A process as claimed in claim 21, wherein the molecular sieve catalyst component (B) is AW-500.

27. A process as claimed in claim 21, wherein the molecular sieve catalyst component (B) is Zeolon-700.

28. A process as claimed in claim 21, wherein the molecular sieve catalyst component (B) is SAPO-11.

29. A process as claimed in claim 22, wherein the molecular sieve catalyst component (B) is LZ-105.

30. A process as claimed in claim 1, wherein component (A) is:

$$Mo_xV_yZ_z$$

wherein Z, (x), (y) and (z) are as defined in claim 1 and component (B) is a palladium-containing oxides catalyst.

31. A process as claimed in claim 6, wherein component (A) is $Mo_aV_bNb_cSb_dX_e$ mixed oxides wherein X, (a), (b), (c), (d) and (e) are as defined in claim 6 and component (B) is a palladium-containing oxides catalyst.

32. A process as claimed in claim 6, wherein component (A) is $$Mo_aV_bNb_cSb_dCa_e$$

mixed oxides wherein (a), (b), (c), (d) and (e) are as defined in claim 6 and component (B) is a palladium-containing oxides catalyst.

33. A process as claimed in claim 32, wherein said gaseous feed comprises ethane, ethylene and oxygen.

34. A process as claimed in claim 32, wherein said gaseous feed comprises ethylene and oxygen.

35. A process as claimed in claim 32, wherein said gaseous feed comprises ethane and oxygen.

36. A process as claimed in claim 32, wherein said component (B) is a $Pd_{0.04}V_{0.68}Sb_{0.28}$ oxides-sulfate catalyst.

37. A process as claimed in claim 36, wherein said gaseous feed comprises ethane, ethylene and oxygen.

38. A process as claimed in claim 36, wherein said gaseous feed comprises ethylene and oxygen.

39. A process as claimed in claim 36, wherein said gaseous feed comprises ethane and oxygen.

40. A process as claimed in claim 32, wherein said component (B) is a $Na_{0.06}Pd_{0.03}H_{0.11}P_{0.07}Mo_{0.68}V_{0.06}$ oxides catalyst.

41. A process as claimed in claim 40, wherein said gaseous feed comprises ethane, ethylene and oxygen.

42. A process as claimed in claim 40, wherein said gaseous feed comprises ethylene and oxygen.

43. A process as claimed in claim 1, wherein component (A) is:

$$Mo_xV_yZ_z$$

wherein Z, (x), (y) and (z) are as defined in claim 1 and component (B) is as tungsten-phosphorus-containing oxides catalyst.

44. A process as claimed in claim 6, wherein component (A) is $Mo_aV_bNb_cSb_dX_e$ mixed oxides wherein X, (a), (b), (c), (d) and (e) are as defined in claim 6 and component (B) is a tungsten-phosphorus-containing oxides catalyst.

45. A process as claimed in claim 6, wherein component (A) is $Mo_aV_bNb_cSb_dCa_e$ mixed oxides wherein (a), (b), (c), (d) and (e) are as defined in claim 6 and component (B) is a tungsten-phosphorus-containing oxides catalyst.

46. A process as claimed in claim 45, wherein said gaseous feed comprises ethane, ethylene and oxygen.

47. A process as claimed in claim 45, wherein said gaseous feed comprises ethylene and oxygen.

48. A process as claimed in claim 45, wherein said gaseous feed comprises ethane and oxygen.

49. A process as claimed in claim 45, wherein said component (B) is a $W_{0.8}P_{0.2}$ oxides catalyst.

50. A process as claimed in claim 49, wherein said gaseous feed comprises ethane, ethylene and oxygen.

51. A process as claimed in claim 45, wherein said component (B) is a $W_{0.38}P_{0.09}Cr_{0.53}$ oxides catalyst.

52. A process as claimed in claim 51, wherein said gaseous feed comprises ethane, ethylene and oxygen.

53. A process as claimed in claim 51, wherein said gaseous feed comprises ethylene and oxygen.

54. A process as claimed in claim 51, wherein said gaseous feed comprises ethylene and oxygen.

55. A process as claimed in claim 1, wherein component A is:

$$Mo_xV_yZ_z$$

wherein Z, (x), (y) and (z) are as defined in claim 1 and component (B) is a tin-molybdenum-containing oxides catalyst.

56. A process as claimed in claim 6, wherein component (A) is $Mo_aV_bNb_cSb_dX_e$ mixed oxides wherein X, (a), (b), (c), (d) and (e) are as defined in claim 6 and component (B) is a tin-molybdenum-containing oxides catalyst.

57. A process as claimed in claim 6, wherein component (A), is $Mo_aV_bNb_cSb_dCa_e$ mixed oxides wherein (a), (b), (c), (d) and (e) are as defined in claim 6 and component (B) is a tin-molybdenum-,containing oxides catalyst.

58. A process as claimed in claim 57, wherein said gaseous feed comprises ethane, ethylene and oxygen.

59. A process as claimed in claim 57, wherein said gaseous feed comprises ethylene and oxygen.

60. A process as claimed in claim 57, wherein said gaseous feed comprises ethane and oxygen.

61. A process as claimed in claim 59, wherein said component (B) is a $Sn_{0.7}Mo_{0.3}$ oxides catalyst.

62. A process as claimed in claim 61, wherein said gaseous feed comprises ethane, ethylene and oxygen.

63. A process as claimed in claim 61, wherein said gaseous feed comprises ethylene and oxygen.

64. A process as claimed in claim 61, wherein said gaseous feed comprises ethane and oxygen.

* * * * *

UNITED STATES PATENT AND TRADEMARK OFFICE
CERTIFICATE OF CORRECTION

PATENT NO. : 5,162,578
DATED : Nov. 10, 1992
INVENTOR(S) : James H. McCain, Jr., et al.

It is certified that error appears in the above-identified patent and that said Letters Patent is hereby corrected as shown below:

Claim 15, line 2, "comprises, ethylene" should read --comprises ethylene--.

Claim 36, line 2, "$Pd_{0\ 04}$" should read --$Pd_{0.04}$--.

Claim 61, line 1, "59" should read --57--.

Signed and Sealed this

Tenth Day of May, 1994

BRUCE LEHMAN

Attest:

Attesting Officer

Commissioner of Patents and Trademarks